(12) United States Patent
Liesfeld et al.

(10) Patent No.: US 8,100,531 B2
(45) Date of Patent: Jan. 24, 2012

(54) OPHTHALMOSCOPE INCLUDING AN ELECTRONIC SHUTTER

(75) Inventors: Ben Liesfeld, Potsdam (DE); Winfried Teiwes, Kleinmachnow (DE); Michael Huppertz, Berlin (DE); Kay-Uwe Amthor, Potsdam (DE)

(73) Assignee: OD-OS GmbH, Teltow (DE)

( * ) Notice: Subject to any disclaimer, the term of this patent is extended or adjusted under 35 U.S.C. 154(b) by 139 days.

(21) Appl. No.: 12/307,677

(22) PCT Filed: Jul. 9, 2007

(86) PCT No.: PCT/EP2007/056967
§ 371 (c)(1),
(2), (4) Date: Jan. 6, 2009

(87) PCT Pub. No.: WO2008/003788
PCT Pub. Date: Jan. 10, 2008

(65) Prior Publication Data
US 2010/0007849 A1    Jan. 14, 2010

(30) Foreign Application Priority Data
Jul. 7, 2006    (EP) .................................... 06116853

(51) Int. Cl.
A61B 3/14    (2006.01)
A61B 3/10    (2006.01)

(52) U.S. Cl. .......................... 351/207; 351/214; 351/221

(58) Field of Classification Search .......... 351/205–207, 351/210, 200, 213–214, 221–223, 246, 240
See application file for complete search history.

(56) References Cited

U.S. PATENT DOCUMENTS

| | | | |
|---|---|---|---|
| 6,758,564 B2 | 7/2004 | Ferguson | |
| 2005/0105044 A1* | 5/2005 | Warden et al. | 351/159 |
| 2006/0114544 A1* | 6/2006 | Bloom et al. | 359/279 |
| 2008/0278683 A1* | 11/2008 | Su et al. | 351/205 |
| 2009/0244482 A1* | 10/2009 | Elsner et al. | 351/206 |

FOREIGN PATENT DOCUMENTS

| | | |
|---|---|---|
| EP | 1389943 B1 | 3/2005 |
| WO | WO9905853 A1 | 2/1999 |
| WO | WO0094088 A2 | 11/2008 |

* cited by examiner

*Primary Examiner* — Dawayne Pinkney
(74) *Attorney, Agent, or Firm* — Faegre & Benson LLP (57) ABSTRACT

An opthalmoscope for examining a patient's eye includes an illumination device for generating an illumination beam Illumination imaging optics image the illumination beam onto the eye and a scanning device scans the illumination beam over the eye. The opthalmoscope also includes an observation device and observation imaging optics for imaging an observation beam generated by reflection of the illumination beam from the eye onto the observation device. An electronic shutter excludes stray light from the observation beam. The observation device comprises an electronic sensor with an array of photosensitive pixels that can respectively be activated and/or read out in rows, and the scanning device includes an electronic drive circuit for reading out at least one pixel row of the sensor.

36 Claims, 8 Drawing Sheets

OPHTHALMOSCOPE INCLUDING AN ELECTRONIC SHUTTER

FIELD OF THE INVENTION

The present invention relates to an opthalmoscope for examining a patient's eye.

BACKGROUND

An opthalmoscope is used to observe the patient's eye background, for example for retinal examinations. An opthalmoscope delivers high-resolution color or black-and-white images in continuous succession, so that it can be used to diagnose the eye as well as for carrying out and documenting therapeutic interventions. Imaging of the eye background, for example the retina, constitutes an optical challenge in this regard since both the illumination and the observation of the eye background is carried out through a comparatively small entry pupil of the eye. The eye background furthermore generally has only a weak reflectivity, which dominates for red color components, so that high-contrast color images of the eye background can in general be produced only by a light source with strong blue and green components.

Optical examination of the eye background with the aid of an illumination beam, which is examined as an observation beam after reflection for example from the retina, is moreover made difficult by undesired further reflections from the interfaces of the cornea as well as by undesired light scattering for example from vitreous body turbidities. All these perturbing light beams, which may be contained in the observation beam but are not attributable to the desired reflection of the illumination beam from the part of the eye to be examined, will be referred to together below as "stray light".

In order to resolve this stray light problem, EP 1389943 B1 discloses an opthalmoscope for examining a patient's eye, comprising, an illumination device for generating an illumination beam, illumination imaging optics for imaging the illumination beam onto the eye, and means for scanning the illumination beam over the eye, as well as an observation device which comprises an electronic sensor with an array of photosensitive pixels, which can respectively be activated and/or read out in rows, observation imaging optics for imaging an observation beam, generated by reflection of the illumination beam from the eye, onto the observation device, and means for excluding stray light from the observation beam.

The illumination device used in this case is particularly a halogen lamp, the light of which is collimated by means of a condenser and focused by the illumination imaging optics onto the patient's eye background. The observation beam reflected by the eye background is imaged by the observation imaging optics onto an image plane, in which there is a CCD sensor as an observation device.

The means for scanning the illumination beam over the eye in this opthalmoscope according to the species are formed by a slit shutter, which oscillates in front of the halogen lamp in the illumination beam collimated by the condenser. This shutter is made of an opaque material, for example a flat metal material and transmits only a linear segment of the illumination beam, which is defined by the size of the slit shutter and is likewise scanned to and fro over the patient's eye at this oscillation frequency.

The means for excluding stray light from the observation beam in this opthalmoscope according to the species are also formed by a mechanically oscillating slit shutter. In particular, EP 1389943 B1 proposes that the slit shutter oscillating in front of the halogen lamp and the slit shutter oscillating in front of the CCD sensor, which in any event must be synchronised with one another for imaging reasons, should be formed as a shutter slit pair in a common metal sheet.

In practice, however, it has been found that particularly the selection of a metal sheet which has a slit shutter and oscillates in front of the sensor leads to problems. This is because on the one hand the oscillations of the mechanical oscillator for the metal sheet can be decoupled only insufficiently from the housing of the instrument, which generally entails difficulties in handling the opthalmoscope and in particular degradations of the image sharpness owing to co-vibration of the sensor.

On the other hand, in order to achieve a maximally compact configuration of the opthalmoscope, the shutter in the observation beam must lie as accurately as possible in the image plane of the observation device and therefore on the sensor. It is nevertheless compulsory to maintain a certain minimum distance of the metal sheet oscillating from the sensor, which inevitably leads to inferior suppression of perturbing stray light.

SUMMARY OF THE INVENTION

An opthalmoscope includes an electronic system for excluding stray light from the observation beam including an electronic drive circuit for reading out at least one pixel row of the sensor The opthalmoscope comprises an electronic control unit which is adapted to control the scanning means and the electronic drive circuit so that the scanning of the illumination beam over the eye is synchronous with the change of the pixel row currently to be read out.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

DETAILED DESCRIPTION

Figure 1:
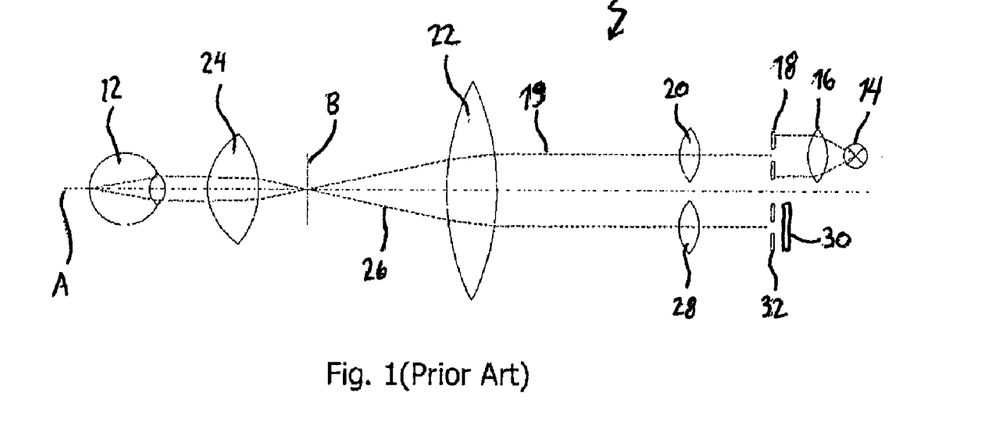
FIG. 1 is a schematic view of an opthalmoscope of the prior art.

FIG. 1 shows a schematic representation of an opthalmoscope 10 of the prior art for studying a patient's eye 12. The light emitted by an illumination device 14 is collimated by means of a condenser 16 and strikes a slit shutter 18 which oscillates, specifically in a direction perpendicular to the optical axis A of the opthalmoscope 10 in the plane of the drawing in the schematic representation of FIG. 1. This slit shutter 18 is oriented perpendicularly to the plane of the drawing.

A line, the length and thickness of which is defined by the shape of the slit shutter 18 and whose position depends on the current location of the oscillating slit shutter, is thereby extracted from the flat light spot onto which the condenser 16 has collimated the light of the illumination device 14.

Using further lenses 20, 22, the illumination beam 19 is focused into an intermediate image plane B, from which it is imaged through an opthalmoscopic lens 24 onto the eye 12. The schematic representation of FIG. 1 in this case shows imaging onto the eye background, for example for a retinal examination.

The observation beam, resulting from reflection of the illumination beam 19 by the eye background, images the eye background through the opthalmoscopic lens 24 into the intermediate image plane B. This intermediate image is focused by means of the further lenses 22, 28 onto a CCD sensor 30. Immediately before reaching the CCD sensor 30, the observation beam 26 must in this case pass through a further slit shutter 32 which oscillates in front of the CCD sensor 30, synchronously with the slit shutter 18 in the beam path of the illumination beam 19.

With the aid of the slit shutter 32, this ensures that essentially only the desired observation beam 26 reaches the CCD sensor 30, while stray light is excluded. Such stray light may, for example, be attributable to reflections from the front side of the eye or scattering by vitreous body turbidities of the eye 12.

It can be seen in FIG. 1 that the oscillating slit shutter 32 is arranged comparatively close to the CCD sensor 30. This is essential, since the suppression of perturbing scattered light will deteriorate with an increasing distance between the slit shutter 32 and the CCD sensor 30. The effect of this proximity, however, is that vibrations may be transmitted from the oscillating slit shutter 32 onto the CCD sensor 30, for example via a housing (not represented in the figures) of the opthalmoscope 10. This leads to fundamental problems in handling the opthalmoscope 10, and in particular it degrades the sharpness of the image of the eye 12 delivered by the CCD sensor 30.

Figure 2:
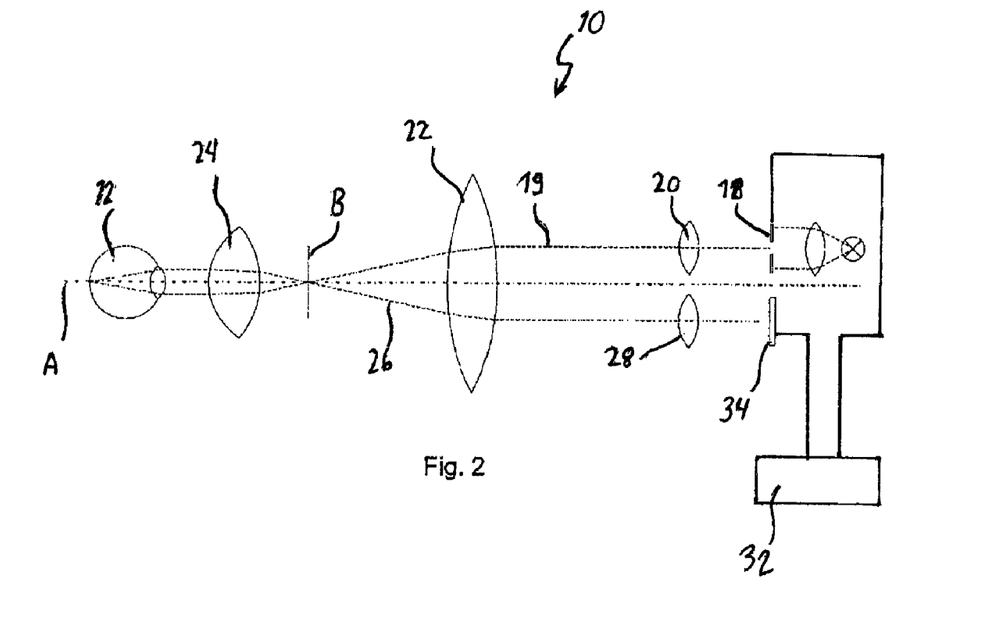
FIG. 2 is a schematic view of an opthalmoscope according to an embodiment of the present invention.

FIG. 2 shows a schematic representation of an opthalmoscope 10 according to an embodiment of the invention. According to the embodiment represented in FIG. 2, the opthalmoscope 10 according to the invention differs from that of the prior art in that an electronic sensor 34, which comprises an array of photosensitive pixels that can respectively be activated and/or read out in rows and can be driven individually by means of an electronic drive circuit, is provided in the observation beam path 26 instead of the CCD sensor 30 and the slit shutter 32 oscillating in front of it. The electronic drive circuit is arranged in the electronic sensor 34 and is not represented in the figures.

Figure 3A:
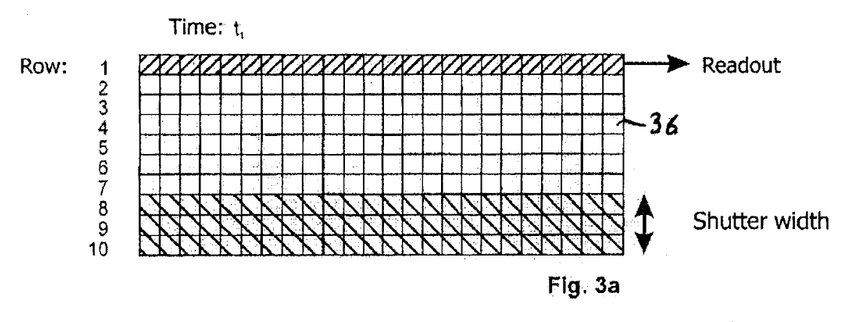
FIGS. 3a-3c show plan views of arrays of photosensitive pixels of an electronic sensor at three different times during a readout process.
Figure 3B:
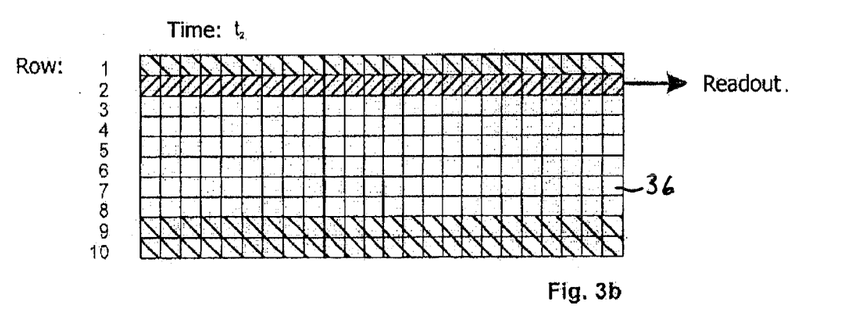
Figure 3C:
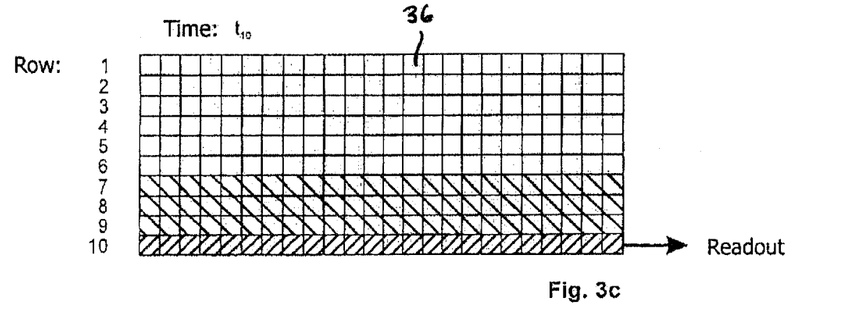

The functionality of the electronic sensor 34 controlled by the electronic drive circuit will be explained below with the aid of FIGS. 3a to 3c:

FIGS. 3a to 3c show a schematic plan view of an array of photosensitive pixels of an electronic sensor 34, represented in a simplified fashion. In the simplified embodiment shown, this array of photosensitive pixels comprises 10 pixel rows in all, which are numbered 1, 2, . . . , 10. Each pixel row in FIGS. 3a to 3c comprises twenty-four pixels, which generate charges by means of photosensitive elements as a function of the incident amount of the light. Each pixel 36 is assigned its own amplifier electronics, which convert the electrical charge generated in the pixel 36 into a respective voltage signal. The functionality of such electronic sensors with so-called "active pixels", in particular CMOS sensors, is known per se and will not be further explained here.

With the aid of the electronic drive circuit provided in the electronic sensor 34, each pixel row can be switched to one of three operating states:
  a) A deactivated mode in which the pixel row does not integrate any charges despite the incidence of light, and does not therefore generate a voltage signal; the pixel rows 2, 3, . . . , 7 are in this deactivated mode in FIG. 3a, which is indicated by blank pixels 36 in these pixel rows.
  b) An active mode in which incidence of light leads to the generation of a continuously rising voltage signal; pixel rows 8, 9 and 10 are in this operating state in FIG. 3a, which is indicated by simple hatching of these pixel rows.
  c) A readout mode in which a pixel row is read out, i.e. the voltage signal built up in a certain preceding exposure time is interrogated by the electronic drive circuit; the pixel row is subsequently erased, i.e. the voltage signal is reset back to the value zero. Only pixel row 1 is in this readout mode in FIG. 3a, indicated by the dense hatching.

Figure 4A:
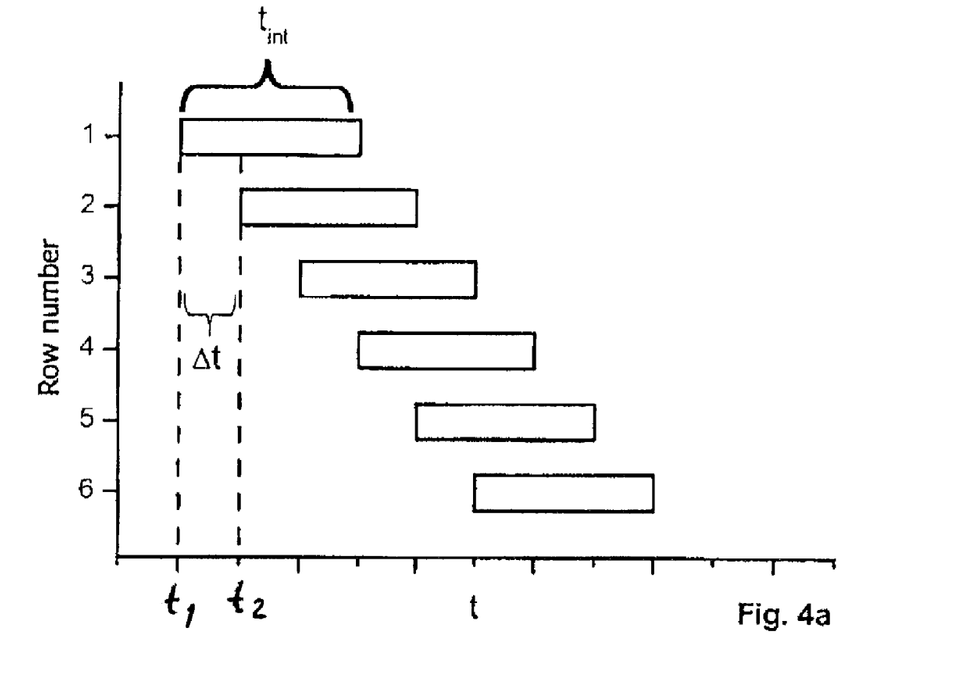
FIG. 4a shows a simplified time diagram describing the exposure time $t_{INT}$ of a pixel row.
Figure 4B:
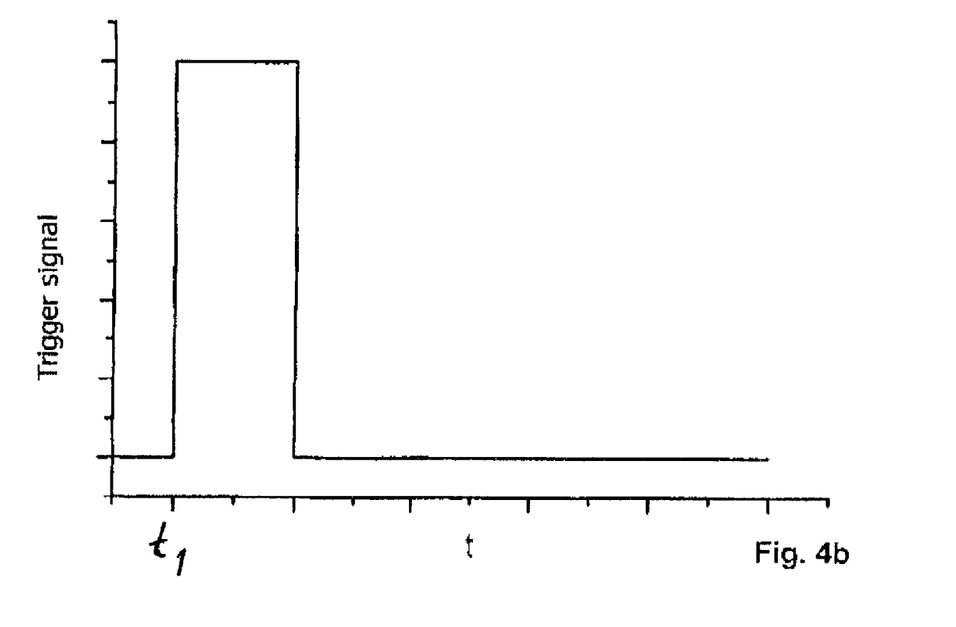
FIG. 4b shows a simplified time diagram of a trigger signal at the start of a readout process of the electronic sensor.

The readout process of the electronic sensor 34, controlled by the electronic drive circuit, will be explained below with the aid of FIGS. 3a to 3c, 4a and 4b:

At a start time $t_1$ indicated in the time diagrams of FIGS. 4a and 4b, the electronic drive circuit receives a trigger signal, for example a TTL signal, from an electronic control unit 38, for example a central control computer. The leading edge of the trigger signal represented in FIG. 4b starts a complete readout cycle of the electronic sensor 34, by pixel row number 1 initially being switched from the inactive state to the readout state and subsequently to the active state, i.e. incidence of light leads to the build-up of a voltage signal in each pixel of the first pixel row. The first pixel row remains in this active state for an exposure time $t_{INT}$, and is read out by the electronic drive circuit at a corresponding instant $t_1$ of the next readout cycle.

After an adjustable time delay $\Delta t$ has elapsed following the start time $t_1$, the second pixel row is also read out and switched to the active state, and so is the third pixel row after a further time delay $\Delta t$. In the case shown in FIG. 4a, $t_{INT}=3\times\Delta t$ is selected so that the second and third pixel rows are currently also in the active mode at the instant $t_4=t_1+t_{INT}=t_1+3\times\Delta t$ when the fourth pixel row is read out and activated, whereas the first pixel row is already deactivated.

After the first pixel row has been read out at the instant $t_1$ it is activated, and the second pixel row, which was exposed for the time $t_{INT}$ starting from the instant $t_1$ of the previous cycle, is read out after a further time delay $\Delta t$ i.e. at an instant $t_2=t_1+\Delta t$. In this way, the readout process respectively advances by one pixel row of the electronic sensor 34 in time intervals corresponding to the time delay $\Delta t$, i.e. from pixel row number 1 through to pixel row number 10 in the example shown in FIGS. 3a to 3c. The effect of selecting $t_{INT}=3\times\Delta t$ is that three neighboring pixel rows, namely the pixel rows n-1, n-2 and n-3, are active at the time when the $n^{th}$ pixel row is read out. This defines the effective width of the electronic slit shutter which, so to speak, moves from top to bottom over the array of photosensitive pixels 36 in FIGS. 3a to 3c. It is necessary to ensure that the voltage built up in a pixel row during the time $t_{INT}$ is not interrogated until the next cycle of the electronic readout, when this pixel row is switched to the readout mode.

The total time T needed for a full cycle corresponds to the product of the number N of pixel rows (in the example of FIGS. 3a to 3c, N=10) and the time delay $\Delta t$, i.e. T $=$N$\times\Delta t$. By selecting the three parameters $\Delta t$, $t_{INT}$ and N, the image repetition rate 1/T and the effective width of the electronic slit shutter can therefore be adjusted more flexibly than the corresponding parameters of a mechanically oscillating slit shutter 32 in the prior art according to FIG. 1.

The electronic control unit 38 is adapted to use the trigger signal, represented in FIG. 4b, in order to synchronize the respectively active pixel rows with the movement of the slit shutter 18 in the illumination beam. At the instant $t_1$ for example (see FIG. 3a), the pixel rows 8, 9 and 10 are active. The instant $t_1$ must therefore be selected so that it corresponds to a time when the slit shutter 18 lies at the lower turning point of its oscillating movement. The sequence of pixel row activation processes represented in FIGS. 3a to 3c and 4a, from the top (in FIG. 3a, pixel row number 1 is read out and then immediately activated) to the bottom (in FIG. 3c, pixel row 10 is read out and thereupon immediately activated), then takes place synchronously with a movement of the slit shutter 18 from top to bottom in FIG. 2.

Since, as shown in FIGS. 3a to 3c and 4a, an electronic shutter constantly travels from top to bottom over the pixel array according to this "rolling shutter" principle, the only images of the electronic sensor 34 which are processed are those which correspond to a downward movement of the illumination beam 19 which is synchronous therewith. Those oscillation phases in which the slit shutter 18 in FIG. 2 moves upwards are not usable. For this reason, after a complete readout cycle of the electronic sensor 34, in which the voltage signals built up in the individual pixel rows in the preceding cycle are read out, the release of the next trigger signal by the electronic control unit 38 is delayed until the slit shutter 18 has again reached its upper turning point.

A further improvement of the image of the eye 12 delivered by the electronic sensor 38 may be achieved not only by synchronizing the readout start time $t_1$ with the upper turning point of the oscillating slit shutter 18, but also by matching the downward movement of the electronic shutter in FIGS. 3a to 3c with the corresponding downward movement of the slit shutter 18 in the illumination beam 19. If for example the slit shutter 18 oscillates sinusoidally in the illumination beam 19, then its speed with which it travels through the illumination beam 18 will respectively be equal to zero at the upper and lower turning points of the oscillation, whereas it reaches a maximum in the middle between the two turning points. This may be taken into account in the electronic sensor 34 by not selecting the time delay $\Delta t$ to be constant, in contrast to FIG. 4a, but instead selecting it to be greater as a function of the respective pixel row at the upper and lower edges of the pixel array (for example in the region of pixel rows 1 and 10) than in the middle of the pixel array (in the vicinity of pixel rows 5 and 6).

This additional electronic outlay, which is entailed when wishing to adapt the movement of the "rolling shutter" of the electronic sensor 34 to the movement of the mechanical slit shutter 18, may be avoided if conversely the time sequence of the electronic shutter as represented in FIGS. 3a to 3c, 4a and 4b is retained and the movement of the mechanical slit shutter is adapted thereto. For example, the electronic control unit 38 may control a driver mechanism (not represented in the figures) of the slit shutter 18 so that the slit shutter 18 executes a kind of "sawtooth" trajectory, i.e. it is moved with a constant speed from its upper turning point to its lower turning point and is subsequently returned much more rapidly to its upper turning point.

Depending on the desired image repetition frequency, such a sawtooth movement of an extended metal sheet, in which the slit shutter 18 is provided, may however prove to be difficult.

Figure 5:
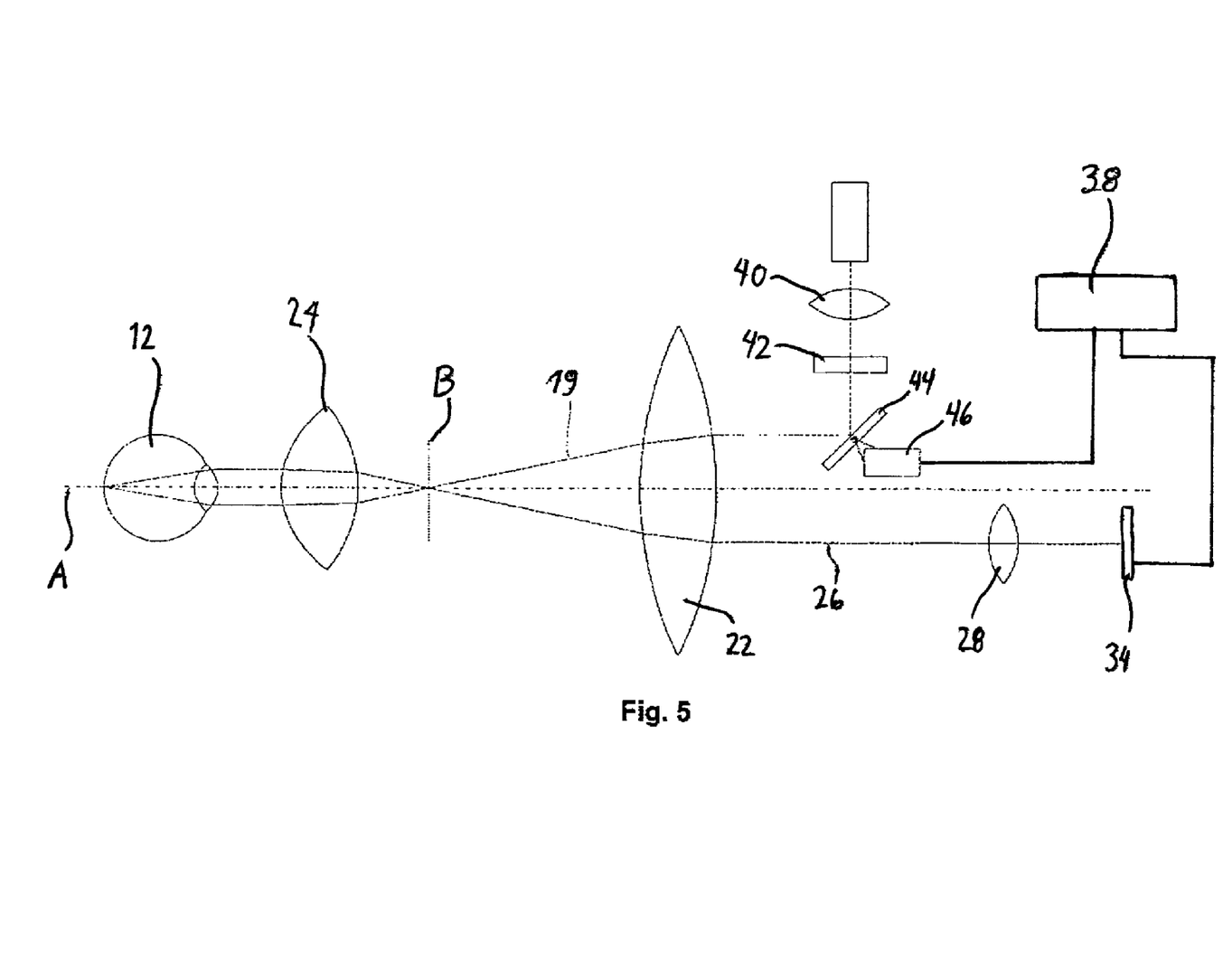
FIG. 5 shows a schematic view of an opthalmoscope according to another embodiment of the present invention with line focusing optics and a tiltably mounted mirror in the illumination beam.

In an embodiment of the opthalmoscope 10 according to the invention as represented in FIG. 5, the generation of the illumination beam 19 is therefore also modified relative to the prior art according to FIG. 1, in the form of line focusing optics in order to facilitate synchronization with the electronic shutter in the electronic sensor 34:

In FIG. 5, components which correspond to those of the embodiment represented in FIG. 2 are provided with the same references. In particular, an electronic sensor 34 having the properties described above is also used to record the observation beam in the preferred embodiment according to FIG. 5.

In this embodiment, however, a point-like light source is used as the illumination device 14, for example a laser or the end of an optical waveguide. The light emerging from it is converted into a parallel beam of rays by a condenser 40 and is directed onto a cylinder lens 42. Arranged behind the cylinder lens 42 in the beam direction, there is a tiltably mounted mirror 44 which reflects the illumination beam 19 approximately parallel to the optical axis A in FIG. 5, leftwards in the direction of the lens 22 which lies in the focusing plane of the cylinder lens 42. The cylinder lens 42 is in this case positioned so that the line focus generated by it is oriented perpendicularly to the plane of the drawing of FIG. 5.

The mirror 44 is mounted tiltably on a scanning device 46, which is driven by the electronic control unit 38 that simultaneously controls the electronic drive circuit of the electronic sensor 34. The electronic control unit 38 is adapted to control the scanning device 46 so that it scans the illumination beam 19 over the eye 12 by rotating the mirror 44 in the plane of the drawing of FIG. 5, synchronously with the movement of the electronic shutter in the electronic sensor 34. With the continuous linear downward travel of the electronic shutter as shown in FIGS. 3a to 3c, the mirror 44 may execute a sawtooth trajectory for example by rotating it anticlockwise in steps starting from the position shown in FIG. 5 and finally, as soon as the electronic shutter in the electronic sensor 34 has reached the lower pixel row, for example pixel row number 10 in FIG. 3c, returning it quickly in the clockwise direction to its starting position according to FIG. 5.

In practice, such a tiltably mounted mirror has a very small moment of inertia, so that it can be used not only at high frequencies but generally in a large frequency range. The combination of such a mirror with a "rolling shutter" according to FIG. 5, which therefore allows free selection of the image repetition rate and external synchronization with the aid of the electronic control unit 38, therefore permits optimal adaptation of the illumination of the eye 12 to the respectively desired observation. Owing to the low inertia of the mirror 44, vibrations are almost entirely avoided in the opthalmoscope 10 according to the invention.

The use of a coherent light source, for example a laser, makes it possible to generate a very narrow illumination slit. If a minimal electronic slit width of a single pixel row is selected at the same time, corresponding to a height of a pixel 36 of about 5 µm, then it is possible to achieve confocal imaging perpendicularly to the extent of the slit and therefore to carry out three-dimensional examinations of the eye.

Figure 6:
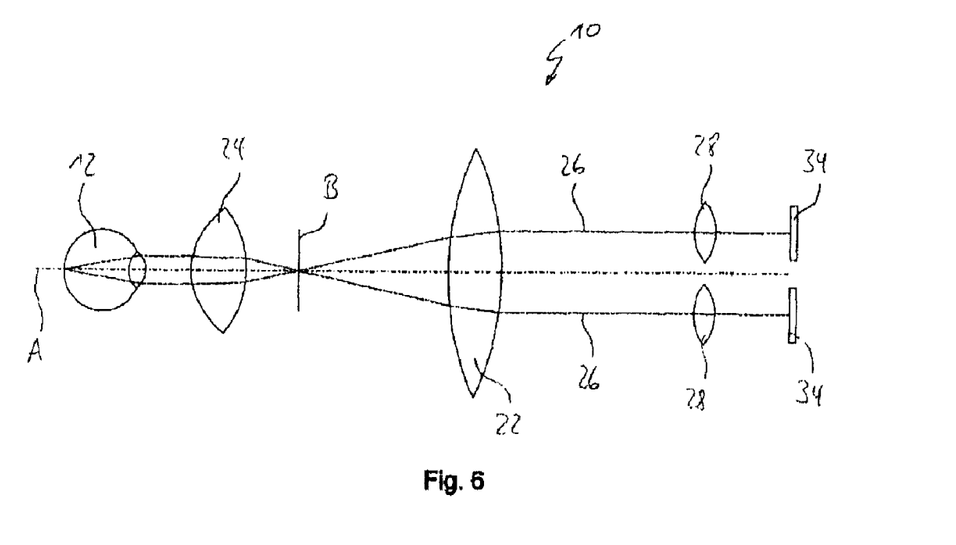
FIG. 6 shows a schematic view of an opthalmoscope according to another embodiment of the present invention with two observation beams for stereoscopic images.

FIG. 6 shows a schematic representation of another embodiment of the opthalmoscope 10 according to the invention with two observation beams 26 for stereoscopic images. The illumination beam path in this case lies outside the plane of the drawing, and is not represented in FIG. 6. Two adjacent electronic sensors 34 are provided in this embodiment, in order to make stereoscopic recordings of the eye 12. The illumination beam path may be selected either as in FIG. 2, i.e. with a slit shutter 18 which oscillates to and fro in front of an illumination device 14, or as shown in FIG. 5, i.e. with line focusing optics in the illumination beam 19. The advantages of the present invention, namely the avoidance of mechanical slit shutters mechanically oscillating, become particularly significant in the embodiment of FIG. 6 because corresponding opthalmoscopes 10 of the prior art with the facility of stereoscopic observation require a total of three slit shutters oscillating, namely one slit shutter in the illumination beam 19 and two slit shutters 32 in the two observation beams which essentially are mutually parallel. Especially in stereoscopic opthalmoscopes 10 of the prior art, this leads to serious vibration problems which are avoided by the invention.

Figure 7:
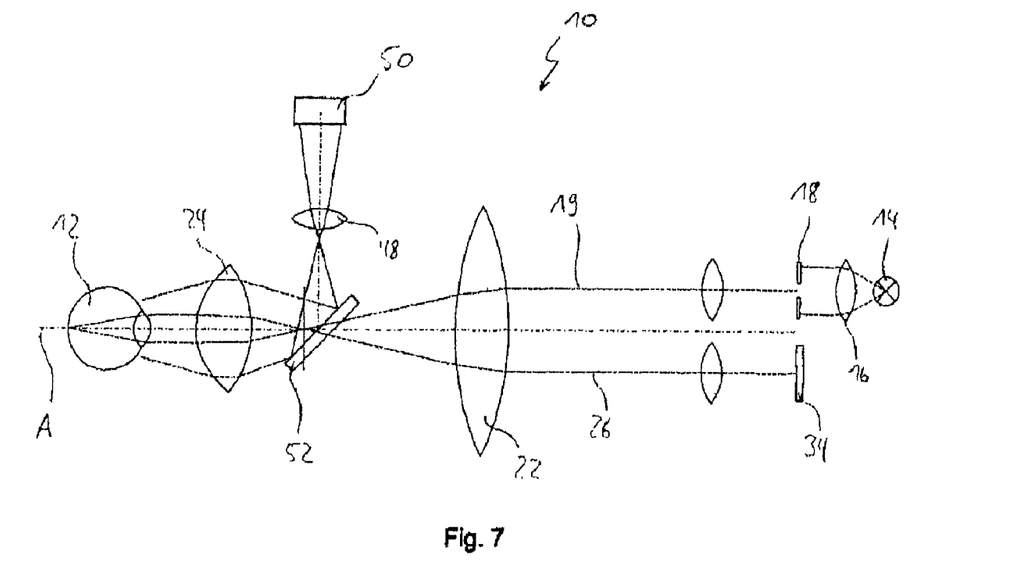
FIG. 7 shows a schematic view of an opthalmoscope according to another embodiment of the present invention for simultaneous examination of the eye foreground.

FIG. 7 shows another embodiment of the opthalmoscope 10 according to the invention with an additional imaging unit, which images the eye foreground through the opthalmoscopic lens 24 and a further lens 48 onto a separate image sensor 50. The separate image sensor 50 is preferably also an electronic sensor with active pixels, for example a CMOS sensor, as was described in detail above.

The beam paths of the eye background and eye foreground illumination are separated by a beam splitter 52 in this embodiment, a pellicle beam splitter preferably being employed.

The eye foreground is illuminated in this embodiment by a separate light source (not represented in FIG. 7), which is positioned directly in front of the eye and ideally emits in the infrared.

In other regards, the embodiment of FIG. 7 corresponds to that of FIG. 2, i.e. with a mechanically oscillating slit shutter 18 in the illumination beam 19. Naturally, the line focusing optics explained with the aid of FIG. 5 may nevertheless also be employed in the embodiment of FIG. 7.

Figure 8:
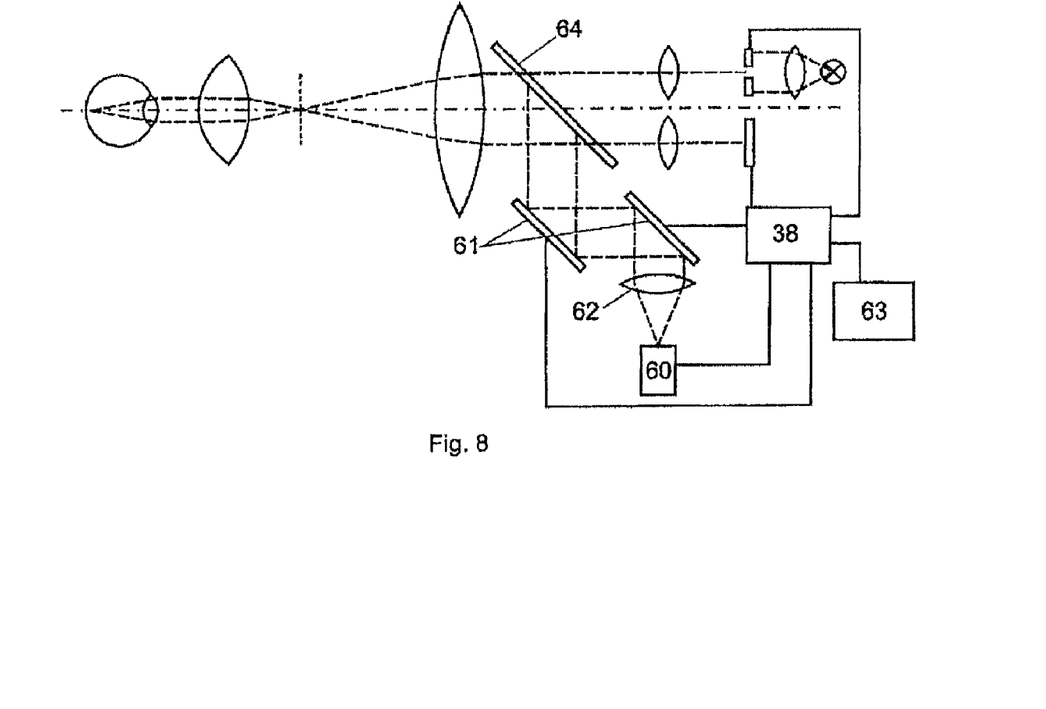
FIG. 8 is a schematic view of an opthalmoscope according to an embodiment of the present invention supplemented with therapy functions.

FIG. 8 shows another embodiment of the opthalmoscope according to the invention which, based on the embodiment of FIG. 2, has been supplemented with therapy functions. To this end a further light source 60 is provided, which generates a therapy light beam that is collimated by means of a lens 62 and is coupled through a beam splitter 64 into the beam path, coaxially with the principal axis of the opthalmoscope. The therapy light beam is in this case deviated by two mirrors 61, which are respectively mounted tiltably about an axis perpendicular to the plane of the drawing of FIG. 8 and an axis lying in the plane of the drawing. The electronic control unit 38 also contains a drive unit, which controls the tilting movements of the mirrors 61 on the basis of setpoint values which a user can input by means of an interface 63, for example a joystick.

Figure 9:
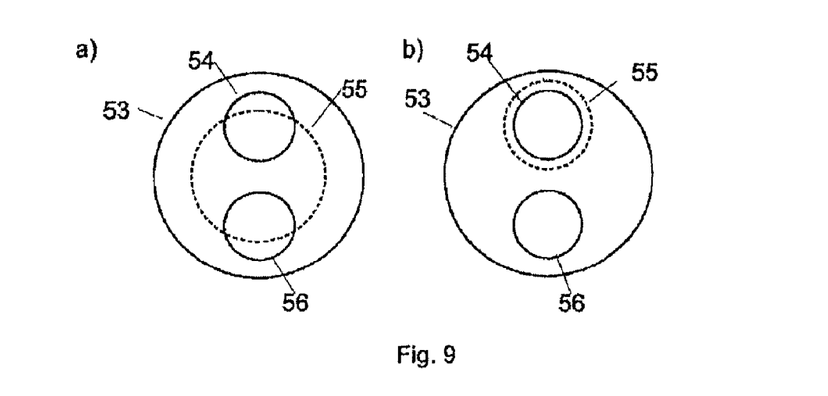
FIGS. 9a and 9b are cross-sectional views of the pupil plane of the human eye when using the opthalmoscope of FIG. 8.

FIG. 9a shows a schematic cross-sectional representation of the pupil plane of a patient's eye in the case of using the opthalmoscope of FIG. 8. Here, reference 53 denotes the pupil of the eye 12, reference 54 denotes the pupil of the illumination beam path, and reference 56 denotes the pupil of the observation beam path. The position of the therapy light beam additionally coupled in with the aid of the beam splitter 64 is indicated by dashes in FIG. 9a, and is denoted by reference 55. In accordance with the input of the therapy light beam in FIG. 8, the therapy light beam 55 lies centrally in FIG. 9a (i.e. on the principal axis of the opthalmoscope 10 according to the invention).

As an alternative, the therapy light beam may also be coupled in decentrally with the aid of the mirror 61 and the beam splitter 64, for example coaxially with the illumination beam path. The corresponding cross-sectional representation of the patient's pupil plane is shown in FIG. 9b.

Figure 10:
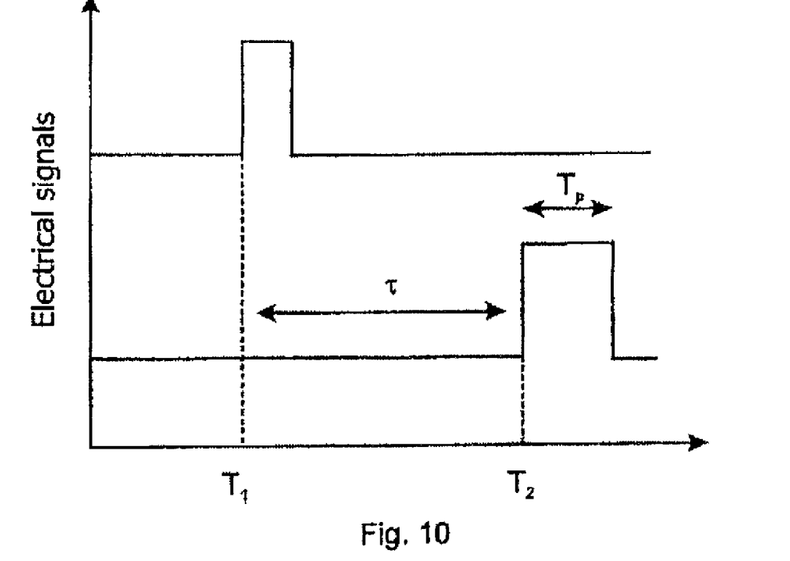
FIG. 10 shows a time diagram which explains the functionality of the activation of the targeting beam as a function of time in the opthalmoscope of FIG. 8.

FIG. 10 shows a time diagram which explains the functionality of the activation of the targeting beam as a function of time. The instant $T_1$ represents the starting point of the shutter movement at one end of the image field. It expediently corresponds to the instant $t_1$ explained above, at which the first pupil row of the electronic sensor 34 is read out. The instant $T_1$ is therefore also defined by the leading edge, represented in FIG. 4b, of a square-wave pulse. After a time delay τ, which as described above may be calculated from the position of the targeting beam spot in the image field (or by values connected therewith), the targeting beam is then activated at an instant $T_2$ for a time $T_p$, which is in turn indicated in FIG. 10 by a square-wave pulse.

Figure 11:
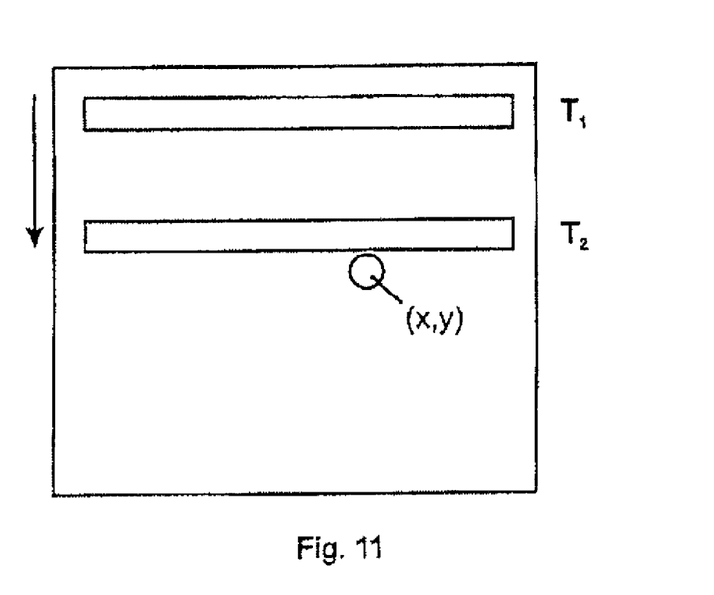
FIG. 11 is a schematic view that represents the sequence, explained in the time diagram of FIG. 10, in the image field.

FIG. 11 represents the sequence, explained in the time diagram of FIG. 10, in the image field. At the instant $T_1$, the shutters are at the starting point of their movement. In FIG. 11, the starting point is represented as lying at the upper edge of the image field. The movement of the shutters takes place downwards over the image field starting from the instant $T_1$, which is indicated by an arrow in the movement direction. At the instant $T_2$, the lower edge of the shutter of the opthalmoscope 10 according to the invention has reached that position (x, y) in the image field where the targeting beam spot lies. At this instant, the targeting beam is then activated for the time $T_p$. Expressed another way, the shining of the targeting beam is restricted to those short periods of time in which the shutters of the opthalmoscope 10 actually permit observation of the desired region of the eye. The targeting beam is switched off outside these short periods of time, so that perturbing reflections are minimized. This pulsed targeting beam is in turn synchronised with the shutters with the aid of the electronic control unit 38.

Figure 12:
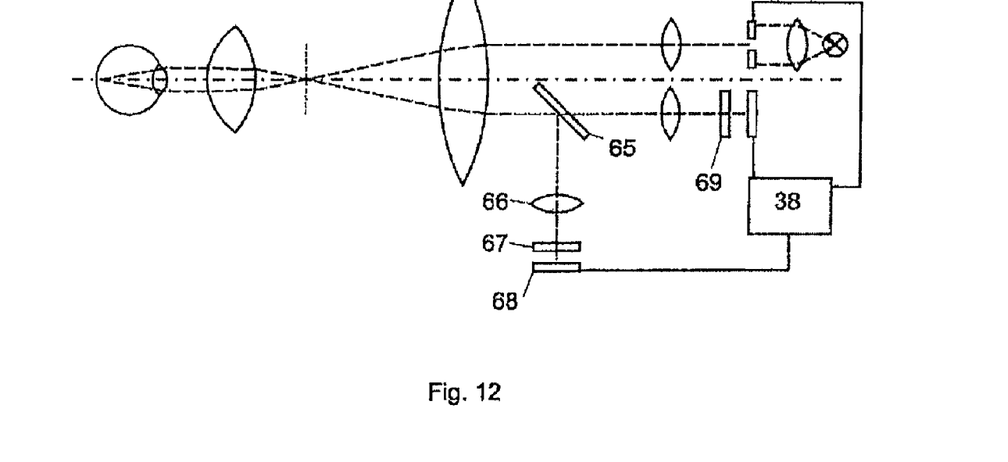
FIG. 12 is a schematic view of an opthalmoscope according to an embodiment of the present invention for the simultaneous measurement of fluorescent emissions.

FIG. 12 shows another embodiment of the opthalmoscope according to the invention for measuring fluorescent emissions. A beam splitter 65, which wavelength-dependently reflects a part of the light coming from the object through a lens 66 onto a second sensor 68, is in this case fitted in the observation beam path. The beam splitter 65 simultaneously functions as a blocking filter for the fluorescence measurement. The filtering effect of the beam splitter may be improved by additional filters in transmission 67 and 69. The electronic control unit 38 in this case contains a drive unit, which ensures that the sensors 68 and 34 are read out synchronously and two images are therefore recorded at the same time.

Figure 13:
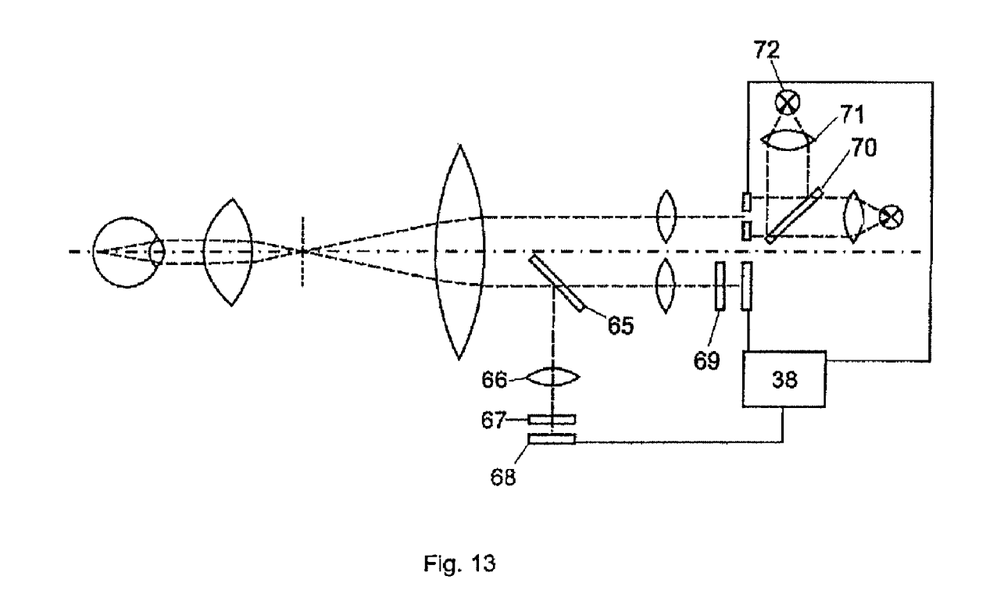
FIG. 13 is a schematic view of an opthalmoscope according to an embodiment of the present invention, in which an additional light source is used to improve the fluorescent light measurement result.

FIG. 13 represents a refinement of the embodiment of FIG. 12, in which an additional light source 72 is used to improve the fluorescence measurement result. The light of this additional light source 72 is collimated via a condenser 71 and is coupled into the illumination beam path through a beam splitter 70. The light source 72 emits light in a wavelength range which lies outside the absorption and emission bands of the fluorescent dye.

The invention is not restricted to the embodiments presented as nonlimiting examples. For example, it is to be understood that the electronic sensor 34 explained with the aid of FIGS. 3a and 3c may comprise in practice more than a thousand pixel rows, rather than just the ten pixel rows shown there for the sake of simplicity.

It is furthermore to be understood that the specific layout of the beam paths of the illumination beam 19 and the observation beam 26, or the observation beams 26 in the case of stereoscopic images, may be varied by known optical elements. It is likewise to be understood that further light beams may be coupled into the proposed beam paths, for example for therapeutic or diagnostic purposes, as is known in principle from the prior art.

In all these modified embodiments, the invention offers not only the above-explained advantages of significantly reducing or entirely eliminating mechanical vibrations due to slit shutters oscillating, but also many other advantages:

a) As already emphasized, the electronic shutter of the electronic sensor 34 lies in its image plane, so that the exclusion of stray light is optimized.

b) Continuous imaging methods demand a sufficiently high image repetition frequency of more than 10 Hz, in order to generate a fluid impression of movement for the observer. The slit shutters used in the prior art therefore have to oscillate with a high frequency, which in practice can be achieved only by a mechanical oscillator in resonance. This in turn demands exact and extremely sensitive tuning, to within small margins, of the natural frequency of the oscillator with the image repetition frequency of the CCD sensor 30. The image repetition frequency is therefore fixed for a given oscillator. In the opthalmoscope 10 according to the invention, however, particularly in the embodiment according to FIG. 5 which functions without any mechanical slit shutter oscillating, there is no such restriction due to a resonance condition.

c) In the opthalmoscope of the prior art, the slit width for a given mechanically oscillating shutter cannot be varied. Many applications, however, require finely graded variation of the slit width and therefore the effective exposure time. For example, variation of the slit width or the image repetition frequency, and therefore the effective exposure time, is desirable to accommodate a wide variety of applications: in angiography of the eye background it is necessary to detect the weak fluorescent emission of a dye, which requires as long an exposure time as possible. This is readily possible by adjusting the parameters of the electronic sensor 34, in particular the parameters N, $\Delta t$ and $t_{INT}$.

d) In the opthalmoscope of the prior art, the frequency of the oscillator for driving the slit shutter is in practice a multiple of the image repetition frequency of the CCD sensor, since mechanical oscillators with a low frequency on the one hand cannot be tuned accurately in their oscillation frequency, and on the other hand they lead to particularly inconvenient vibrations of the entire equipment. This causes double exposures on the CCD sensor 30 and therefore image blurring and motion artifacts due to rapid movement of the eye 12 or other objects being examined. The use of image sensors that combine two image half frames, which are recorded at different instants, to form a full image frame (interlacing) according to one of the conventional video standards (PAL, NTSC), has proven particularly disadvantageous. The further computer-assisted processing and evaluation of the images (for example determining the position, size, shape etc. of blood vessels in the eye 12) is made difficult by such motion artifacts or interlacing artifacts. The inventive avoidance of the mechanical slit shutter in front of the sensor resolves all these problems.

e) The mechanical oscillator oscillating in resonance to drive the slit shutters in the opthalmoscope according to the prior art generally performs a sinusoidal movement. The amount of light integrally striking the eye 12 through the oscillating shutter during a period is therefore distributed nonuniformly over the eye 12, and this leads to a nonuniform contrast and brightness distribution in the image. In order to obtain uniform illumination of the image section despite this, the amplitude of the oscillation is often increased to such an extent that only the approximately linear component of the shutter trajectory lies in the field of view. Only a fraction of the light incident on the eye 12 is therefore used for the imaging, however, which leads to a reduction in the sensitivity of the opthalmoscope 10. In the opthalmoscope 10 according to the invention, conversely, the available light is utilized much better.

f) When using a conventional light bulb or a halogen lamp, which uniformly illuminates the image plane of the illumination beam path, the available luminance of the illumination device 14 is utilized only inefficiently. The thermal radiation of the illumination device 14 leads to a further difficulty in handling the equipment. This problem can be avoided in the embodiment shown in FIG. 5 by a laser and line focusing optics.

g) A halogen lamp, as is used in the prior art, emits a broad thermal frequency spectrum whose maximum lies in the infrared range, and which falls off at shorter wavelengths. Such a light source is therefore unsuitable for generating a high-contrast color image of the eye background, since the eye background reflects primarily in the red spectral range. Semiconductor-based image sensors are furthermore more strongly sensitive in the red and infrared spectral ranges than at shorter wavelengths. A color image of the eye background, recorded with halogen illumination, therefore has a dominant red channel but only weakly pronounced green and blue channels. The image is therefore noisy and low in contrast. Although the use of filters to influence the illumination spectra does improve the color impression, it nevertheless greatly reduces the luminance of the light source. For the aforementioned observation of fluorescent emissions, however, intense excitation of the dyes in a narrow spectral range is necessary. This may be achieved in the embodiment according to FIG. 5 by modern light sources, for example LEDs or lasers.

The use of such an electronic sensor in an opthalmoscope makes it possible to replace the mechanical shutter employed in the prior art by a so-called electronic shutter ("rolling shutter"). This is because with the aid of the electronic drive circuit, all the pixel rows of such a sensor can be activated, deactivated and read out simultaneously in a controlled way. When a pixel is in the activated state, incidence of light leads to the continuous generation of charges which are converted into a voltage signal in a CMOS sensor by means of the amplifier electronics assigned to the respective pixel. Such build-up of voltage is however prevented in the deactivated state, and the pixel or even the entire pixel row is "switched off".

By deliberately activating at least one pixel row in a particular region of the array of photosensitive pixels and simultaneously deactivating all the other pixel rows, the same result as with the aid of a mechanical slit shutter can therefore be achieved electronically. In the opthalmoscope according to embodiments of the invention, stray light can therefore be excluded from the observation beam without this requiring a mechanically oscillating metal sheet with a slit shutter in front of the observation device. Furthermore, in contrast to the mechanical shutter, the electronic shutter provided in accordance with the invention lies not in front of but in the image plane of the observation device, which improves the suppression of stray light.

The electronic drive circuit is adapted respectively to read out a single row. An extremely fine resolution of the electronic sensor can be achieved in this way, which corresponds to a height of about 5 μm with typical CMOS sensors. It would nevertheless in principle be conceivable to combine a plurality of pixel rows, in particular neighboring pixel rows, with the aid of the electronic drive circuit, i.e. always to activate, deactivate or read them out together, and therefore improve the luminous efficiency at the cost of the resolution.

The electronic drive circuit is adapted to change the current pixel row to be read out, in particular from one pixel row to a neighboring pixel row, respectively after an adjustable time delay ($\Delta t$) has elapsed. In an alternative embodiment, in which immediately neighboring pixel rows are read out successively, the electronic drive circuit therefore requires a total time $T=N \times \Delta T$ for a complete cycle, i.e. full readout of the electronic sensor with N pixel rows. The parameter N, which describes the number of pixel rows of the sensor, may in this case be reduced from an upper limit dictated by the design of the sensor by using the above-described electronic combination of neighboring pixel rows, while at the same time the time delay parameter $\Delta T$ may be freely adjusted by the operator of the opthalmoscope according to the invention. The total time required for a full readout cycle may in this way be adjusted, according to the setting of the oscillation period or the oscillation frequency of the mechanical slit shutter provided in the opthalmoscope.

In one embodiment of the invention, the electronic drive circuit is furthermore adapted to activate each pixel row for an adjustable exposure time ($t_{INT}$) before it is read out. The effect achievable by setting this exposure time $t_{INT}$ as a multiple of the time delay $\Delta T$ is therefore that each pixel row is exposed for a longer time, during which it approaches the pixel row currently to be read out. In this way, the effective width of the electronic slit shutter can be adjusted flexibly.

Expediently, the electronic drive circuit is adapted to start the readout process in response to an external trigger signal. In this way it is possible to ensure the synchronization of the shutter for the observation device with the means for scanning the illumination beam. For example, a central control computer for the opthalmoscope according to the invention may control on the one hand the electronic drive circuit of the electronic sensor with the aid of this trigger signal and, on the other hand, a driver for a mechanical slit shutter in the illumination beam.

In principle, synchronization of the electronic shutter in the observation beam with a mechanical shutter in the illumination beam may readily be achieved with the aid of such a central control computer. The central control computer may of course also be part of the electronic sensor or part of the illumination device.

Moreover, the means for scanning the illumination beam over the eye may comprise a tiltably mounted mirror with a scanning device. In order to ensure that the illumination beam striking the tiltably mounted mirror already has the desired line shape, either the opthalmoscope according to the invention may furthermore comprise a fixed slit shutter for extracting a linear illumination beam or it may furthermore comprise line focusing optics for focusing the illumination beam in a line, in which latter case the line focusing optics expediently comprise a cylinder lens. The use of such a tiltably mounted mirror, which is driven with the aid of a galvanometer drive and is employed in an opthalmoscope in order to scan an illumination beam delivered by line focusing optics, is also described in U.S. Pat. No. 6,758,564 B2 to which reference is made in this regard.

For central control of the components of the opthalmoscope according to the invention, it is expedient that the electronic control unit should be adapted to control the electronic drive circuit of the electronic sensor and the scanning device of the tiltable mirror. By transmitting the aforementioned trigger signal to the electronic drive circuit of the electronic sensor, the electronic control unit may then ensure that, for example with a sinusoidally oscillating mirror, the readout process in the electronic sensor begins at a suitable time, for example by reading out the upper pixel row of the electronic sensor as soon as the oscillating mirror has reached its upper turning point.

In this refinement of the opthalmoscope according to the invention, the electronic control unit is adapted to control the scanning device and the electronic drive circuit so that the illumination beam is scanned over the eye synchronously with the change of the pixel row currently to be read out. For example, the electronic control unit may impart a sawtooth trajectory to the scanning device, which corresponds exactly to the movement of the electronic slit in the electronic sensor.

For particularly precise examinations of the patient's eye with a particularly high spatial resolution, it is proposed that the thickness of the line of the focused illumination beam should correspond to the height of the pixel row of the electronic sensor. Confocal imaging of the eye is thereby achieved, so that three-dimensional information about the observed object can be obtained.

When using the said line focusing optics, the illumination device may expediently be a laser. As an alternative, any other form of an essentially point-like illumination device may be used, for example one end of an illuminated optical waveguide.

According to one refinement of the invention, the observation device comprises two electronic sensors for stereoscopic examination of the eye. The advantages of the invention become particularly significant in such an embodiment, since stereoscopic observation with two observation devices in the prior art in fact requires a total of three slit shutters oscillating, which according to the invention may be obviated substantially or even entirely by using the line focusing optics.

Furthermore, according to another embodiment of the invention, the opthalmoscope comprises a separate light source and a separate image sensor for examining the eye. In particular, with the aid of the illumination device, the illumination imaging optics, the observation imaging optics and the observation device, it is in this case possible to examine the eye background, for example the retina of the eye, while the additional imaging unit is used to examine the eye foreground. This may be utilized both for medical examination of the eye foreground per se and for automatic positioning of the patient's eye, as well as for tracking the eye movements of the entire eye with the aid of information which, for example, is obtained by reflection of a light beam from the eye foreground. In particular when adding up the eye background images for angiography, it is advantageous that eye movements which have occurred between the individual images of the eye background can be established by means of such simultaneous observation of the eye foreground.

The opthalmoscope according to the invention may advantageously be supplemented with therapy functions. An important form of therapy in eye medicine for the treatment of diseases such as diabetic retinopathy or age-related macular degeneration, is the thermal action by light on tissue regions to be treated, for example photodynamic therapy (PDT), photocoagulation of tissue or modern methods such as selective retina therapy (SRT) and therapy below the coagulation threshold (sub-threshold therapy, STT). In all these forms of therapy, an intense light pulse is focused onto a special zone of the retina. When carrying out the therapy, it is necessary to ensure that important zones of the eye background (for example the macula) are not inadvertently damaged.

For this type of therapeutic intervention, besides a live image of the eye background, the treating doctor therefore also requires very precise control of the position of the therapy light beam. A targeting beam is typically superimposed coaxially on the therapy light beam as an aid for positioning the therapy light beam. This is always visible to the doctor, but it has a different wavelength and a much lower intensity than the therapy light beam and it does not therefore lead to modifications of the eye background. Reflections from the various interfaces of the eye, which are generated by the light source for illuminating the eye background as well as by the targeting beam, do however make control much more difficult.

An opthalmoscope which generates a reflection-free live image of the eye background and simultaneously projects a therapy beam, on which a targeting beam with a different wavelength is generally superimposed, onto the eye background, constitutes an important instrument for eye medicine. It allows the doctor to be assisted by a computer, for example for navigation over the eye background in order to position the photocoagulation point. Such computer assistance is already prior art in other fields of medicine (for example minimally invasive surgery or neurosurgery). In eye medicine, its implementation has previously been prevented by the lack of observation and treatment instruments. The present invention can remedy these technical deficiencies.

The therapeutic intervention may furthermore be documented objectively by computer assistance. To date this has been possible only approximately, for example with the retina being heated by the light pulse during photocoagulation so as to cause a permanent and clearly visible modification of the tissue. The effect of this is that the destroyed tissue areas, and therefore the loss of vision after the therapy, are usually much greater than is medically necessary. Modern treatments such as PDT, SRT and STT are specifically intended to avoid such visible damage to the retina. Without the documentation method made possible by the present invention, quality assurance is not possible for these therapies.

A slit lamp, onto which a photocoagulation laser is adapted with corresponding input optics, is typically used for treatment of the retina with intense light pulses. A slit lamp is a stereomicroscope with variable slit illumination, the microscope as well as the illumination being mounted rotatably about a common axis in a plane.

In order to observe the eye background, the user holds an opthalmoscopic lens or a contact glass by hand in front of or on the patient's eye. The therapy laser system usually consists of the coaxial combination of a targeting beam and a therapy beam, which expediently have different wavelengths in order to make it easier to distinguish them. The therapy beam is generally input coaxially with the observation beam path between the microscope and the opthalmoscopic lens.

It is therefore inevitable that particularly the targeting beam will generate strong reflections at the various interfaces between the slit lamp and the eye background, which will be seen as interference by the observer. These reflections are very much brighter than the light reflected by the eye background, and the observer can only move them to the edge of the image field laboriously by skilful movement/alignment of the microscope and the opthalmoscopic lens, or else the observer must simply tolerate them. In principle, reflections from interfaces of the human eye cannot be avoided by technical means (i.e. by blooming the surfaces).

However, the said reflections of the targeting beam not only hinder the work of the operator looking through the eyepiece of the microscope, but may also compromise or prevent the use of systems which record images of the eye background with the aid of electronic sensors and which are intended to aid the user during the therapy by computer-assisted evaluation.

In another embodiment, the present invention alleviates the existing restrictions/disadvantages of the prior art by providing a device for projecting a targeting beam and a therapy beam, which also allows reflection-free observation of the eye background by the targeting beam projected onto it. A targeting beam that does not need to be polarized is used, which reduces the costs for the light sources and the optics being employed. Reflections which may be caused by the targeting beam are fully suppressed. Only a single detector is required in this case for tracking the targeting beam on the object.

In the present invention, the therapy beam, with the targeting beam superimposed on it, is coupled into the beam path of the instrument with the aid of a beam splitter. The therapy beam may in this case be arranged coaxially with the illumination beam path or coaxially with the principal axis of the instrument. It must not however be coaxial with the observation beam path since this conflicts with the principle of suppressing reflections which is employed, based on separating the beam paths in the pupil plane of the eye. The effect of separating the beam paths is that the image of a reflection due to the targeting beam at an optical interface between the sensor and object planes is not formed at the same position on the sensor as the image of the targeting beam spot generated on the object (here: the eye background).

The beam splitter may expediently be rendered highly reflective for the wavelength of the therapy beam, but partially transparent for the wavelength of the targeting beam. In this way, only light of the targeting beam reaches the detector and light of the therapy beam does not. As an alternative, the beam splitter may be configured wavelength-independently and an additional selective filter may be used in the observation beam path, which suppresses the light of the therapy beam. Undesired reflections and stray light, which are due to the targeting beam, are suppressed by operating the targeting beam in pulses.

Considering a fixed point on the object, onto which the targeting beam is directed, the targeting beam is only switched on for the time $T_p$ exactly at the instant $T_2$ when the observation shutter of the confocal imaging system is passing over precisely this object point. The activation of the targeting beam is synchronized with the confocal shutter arrangement by a drive unit. This drive unit has information about the respective position of the targeting beam spot on the object and about the start time of the shutter movement. This drive unit is preferably the same as the drive unit which synchronizes the illumination and observation shutter movements.

This may for example be achieved by the drive unit receiving an analogue or digital position signal of the control mirror of the targeting beam and a synchronization pulse of the shutter movement. The position of the targeting beam spot on the object may, for example, be known a priori from the position of one or more deviating mirrors which determine the angular excursion of the targeting beam. From the position (x, y) of the targeting beam and the speed v of the shutter movement, it is possible to calculate a time delay $\tau=y/v$ (for movement of the shutter in the y direction) between the start time of the shutter movement and the activation of the targeting beam, and to convert this into a corresponding, expediently square-wave pulse sequence. When the targeting beam moves on the object, the time delay is adapted according to the position.

The device according to embodiments of the invention imposes minimal requirements on the therapy and targeting beam sources being used. The sources employed need not necessarily be polarized and the pulse operation, which takes place according to the invention on a timescale of 100 μs-10 ms, is known per se.

In another advantageous embodiment of the invention, a drive unit is used which evaluates the images recorded by the instrument according to the invention with the sensor, particularly in real-time. This drive unit performs one or more of the following functions:

Detecting or determining a coordinate system which is stationary on the object, i.e. object-referenced, with the aid of structures on the object in the images recorded by the device according to the invention, or on images of the same object which have been recorded by other devices, Determining the position of the targeting beam in this object-referenced coordinate system, Positioning the targeting beam spot on the eye background according to instructions by the user via a suitable interface (for example a joystick), using one or more suitable deviating mirrors which the drive unit can adjust, Positioning the targeting beam spot without direct intervention by the user, using one or more suitable deviating mirrors which the drive unit can adjust, Enabling or preventing the triggering of a therapy beam pulse, Controlling the parameters of the therapy beam pulse (for example the pulse duration, pulse repetition rate, light power etc. in the case of photocoagulation), Measuring the duration, intensity and frequency of the therapy light pulses, Storing the control parameters of the therapy light pulses and storing the measured values.

By performing these functions, the following methods are possible in conjunction with a suitable display (for example a monitor screen):

The user defines regions (zones) in the object-referenced coordinate system on the object, where the application of therapy light pulses is generally permitted or generally prevented by the drive unit. This may be done with the aid of a single image previously recorded by the equipment according to the invention, or by using images from other equipment according to the prior art. To this end, the drive unit determines in real-time the position of the targeting beam in the object-referenced coordinate system and compares the position with the predetermined regions, and as appropriate enables or prevents the triggering of a therapy light pulse. In another embodiment, the drive unit carries out the definition of the aforementioned zones automatically by analyzing the image.

The drive unit superimposes information onto the display of the live image, the transformations of the position of the superimposed information being compensated for relative to the live image, i.e. both the position of the superimposed information and the live image are based on the same object-referenced coordinate system. The superimposition may be carried out by a rapid image change or by contrast-based overlaying. The information may for example consist of images of the object, which have been recorded at an earlier time or by using different imaging methods with another instrument, or graphical representations compiled by the user in the object coordinate system at a different time.

The user establishes one or more positions, where a therapy light pulse is intended to be applied, in the object-referenced coordinate system on a reference image (target positions). The drive unit then assists the application of a therapy light pulse onto a predetermined position in the object-referenced coordinate system of the object.

While the user is adjusting the position of the targeting beam manually, the drive unit displays the target position in the object-referenced coordinate system as superimposed information in the live image.

The drive unit enables the triggering of a therapy light pulse whenever the user has steered the targeting beam onto the target position with an accuracy established a priori.

The drive unit automatically triggers a light pulse whenever it has steered the targeting beam automatically onto the target position in the object-referenced coordinate system.

The drive unit generates a pattern of two or more targeting beam spots on the eye background by moving and activating the target in a suitable way synchronized with the movement of the observation shutter. The position of the pattern on the eye background is determined by the user via an interface, or is set automatically by the drive unit without intervention from the user. The triggering of the therapy light pulse then takes place at the positions of the pattern generated by the targeting beam. Application of therapy light pulses in such patterns increases the regularity of the pulse placement on the eye background and therefore the reproducibility of the therapy result. In another embodiment of the invention, a pattern is not generated physically on the eye background, but is merely superimposed virtually on the displayed live image. The movement of the virtual pattern is in this case coupled with the movement of the targeting beam spot on the eye background.

The drive unit performs stabilization of the live image with respect to the coordinate system of the object and the display, i.e. the object coordinate system is kept fixed with reference to the coordinate system of the display.

The drive unit performs stabilization of the targeting beam spot in the object coordinate system, i.e. the drive unit moves the targeting beam in a suitable way so that it executes the same relative movements as the object.

The drive unit carries out simultaneous stabilization of the live image with the coordinate system of the display and stabilization of the targeting beam spot in the object coordinate system.

While a therapeutic measure is being carried out by means of the therapy light beam, the drive unit stores the intervention sites (the coordinates in the object-referenced coordinate system where light pulses have been applied) and the parameters of the therapy light pulses (such as pulse duration, light power etc.), so that this information can be displayed at any time by once more superimposing the stored information on live or static images, even when there are no visible traces of the action of light on the object.

After application of a therapy light pulse, the drive unit evaluates either the reflectivity of the tissue at the position of the therapy light action by means of image processing, or another measurement value which is correlated with the temperature of the tissue during the therapy light pulse action and therefore the therapeutic effect, and it modifies the parameters of the therapy light source in a suitable way for the next therapy light pulse. In another embodiment, the evaluation is carried out by means of image processing or the evaluation of a suitable measurement value during the application of a therapy light pulse, and it terminates the therapy light pulse action as soon as a desired status of the tissue is reached.

In addition or as an alternative to the therapy functions described above, the opthalmoscope according to embodiments of the invention may moreover be extended with a view to carrying out fluorescence measurements as will be explained below.

Besides generating simple color images of the retina, opthalmoscopes are also used for more complex imaging methods, for example qualitative detection of the fluorescence of a dye which has been introduced into the patient's bloodstream, in the vessels of the retina. The particular challenge in this field consists in detecting the weak fluorescence by optics whose geometrical optical flux is limited by the special conditions when observing the eye background. A particular difficulty consists in detecting the fluorescence of dyes (for example lipofuscin) naturally present in the human eye and their spatial distribution, the concentration and therefore the luminosity of which dyes after fluorescent excitation is generally very low.

In general, two filters are used for a fluorescence measurement with a broadband light source: an excitation filter for the illumination and a blocking filter for the observation. When a narrowband light source is used (for example a laser, LED), the excitation filter may be obviated. The transmission curves of the filters are configured so that their maximum transmission coincides with the maxima of the absorption or emission curves of the dyes. At the same time, however, the blocking filter must efficiently suppress all of the excitation light in order to obtain a high signal-to-noise ratio.

The fluorescent signal of an object is generally orders of magnitude less than, for example, the excitation light scattered by the object according to Lambert's law. A weak measurement signal entails the need for expensive and sensitive sensors, which therefore necessarily have a low resolution. On the other hand, especially in the field of eye medicine, the incidence of a light onto the object cannot be increased arbitrarily, rather there are critically low limit values precisely at shorter visible wavelengths.

The conventional method of increasing the signal-to-noise ratio in image processing, by averaging a plurality of images (measurements), cannot be generally employed in eye medicine since the object, i.e. the human eye, moves during the observation. Registering a plurality of images in succession, i.e. determining the transformations which have taken place between individual images of a series of images, could allow averaging. For the special application of fluorescence measurement in the human eye, however, the use of such technology is not possible since the fluorescent images are not very pronounced and are very noisy, owing to the weak signal.

The refinement of the invention as proposed here is particularly suitable for compiling fluorescence measurements of the eye background, since it expediently makes it possible to average possibly very noisy images of moving objects. In a fluorescence measuring device according to the prior art, the majority of the light coming from the object to be observed is absorbed or reflected by the blocking filter.

In an advantageous embodiment of the invention, the light of the excitation light source is used to improve the measurement signals. To this end a dichroic beam splitter, which splits the light coming from the object into the shortwave component of the excitation light and the longwave component of the fluorescent emission, is fitted into the observation beam path. The reflected light is in this case imaged onto an additional sensor.

The sensors are operated in a chronologically synchronized fashion, i.e. they function with the same image repetition frequency and they start the integration time of an image at the same instant. Chronologically synchronous image pairs can therefore be recorded. The fluorescent image is in general poorly pronounced in this case, while the image of the scattered excitation light is substantially more pronounced. It is therefore comparatively easy for the geometrical transformations, which have resulted from the movements of the object between the individual images of a series of images, to be calculated from the image of the excitation light. The inverse transformations are then applied to the fluorescent images, so that these can be averaged by addition. Ideally, the signal-to-noise ratio can be improved by a factor of $\sqrt{2}$ with each image pair by this method.

Another advantageous embodiment of the invention uses the light of an additional light source, which emits in a wavelength range that lies outside the absorption and emission bands of the fluorescent object. This additional light source is expediently coupled into the illumination beam path. A dichroic beam splitter which splits the light coming from the object into the shortwave component of the excitation light and the light of the additional light source on the one hand, and the longwave component of the fluorescent emission on the other hand, is now fitted into the observation beam path.

The use of an additional light source offers the advantage that, irrespective of the requirements of the fluorescence measurement, the wavelength may be freely selected outside the absorption and emission bands and expediently selected in a wavelength range which allows stronger exposure of the eye. The images which are used to determine the geometrical transformations are more pronounced owing to the high light intensity, so that the averaging of the fluorescence measurements can be carried out more accurately.

The invention claimed is:
1. An ophthalmoscope for examining a patient's eye, the ophthalmoscope comprising:
an illumination device for generating an illumination beam;
illumination imaging optics for imaging the illumination beam onto the eye;
a scanning device for scanning the illumination beam over the eye;
an observation device which comprises an electronic sensor with an array of photosensitive pixels, which can respectively be activated and/or read out in rows;
observation imaging optics for imaging an observation beam, generated by reflection of the illumination beam from the eye, onto the observation device;

an electronic shutter for excluding stray light from the observation beam, including an electronic drive circuit for reading out at least one pixel row of the sensor, wherein the ophthalmoscope comprises an electronic control unit which is adapted to control the scanning device and the electronic drive circuit so that the scanning of the illumination beam over the eye is synchronous with the change of the pixel row currently to be read out;

an optical system for projecting an additional beam onto a background of the eye in a separate beam path;

one or more tiltable mirrors that are arranged such that translation of the additional beam on the background of the eye can be achieved by tilting one or more of the tiltable mirrors respectively about one or more axes; and a drive unit for driving the one or more tiltable mirrors, wherein the drive unit is adapted to determine a time window, in which the additional beam is switched on from a quantity that correlates a position of a spot generated by the additional light beam in an image field to a start time of shutter movement.

2. The ophthalmoscope according to claim 1, wherein the electronic drive circuit is adapted to read out a single row.

3. The ophthalmoscope according to claim 2, wherein the electronic drive circuit is adapted to change the current pixel row to be read out from one pixel row to a neighboring pixel row after an adjustable time delay has elapsed.

4. The ophthalmoscope according to claim 1, wherein the electronic drive circuit is further adapted to activate each pixel row for an adjustable exposure time before it is read out.

5. The ophthalmoscope according to claim 1, wherein the electronic drive circuit is adapted to start reading out at least one pixel row of the sensor in response to an external trigger signal.

6. The ophthalmoscope according to claim 1, wherein the scanning device further comprises a tiltably mounted mirror.

7. The ophthalmoscope according to claim 6, and further comprising:
a fixed slit shutter for extracting a linear illumination beam.

8. The ophthalmoscope according to claim 6, and further comprising:
line focusing optics for focusing the illumination beam in a line.

9. The ophthalmoscope according to claim 8, wherein the line focusing optics comprise a cylinder lens.

10. The ophthalmoscope according to claim 8, wherein the illumination device is a laser.

11. The ophthalmoscope according to claim 6, wherein the electronic control unit is adapted to control the electronic drive circuit of the electronic sensor and the scanning device of the tiltable mirror.

12. The ophthalmoscope according to claim 11, wherein a thickness of the focused illumination beam corresponds to a height of a pixel row of the electronic sensor.

13. The ophthalmoscope according to claim 1, wherein the observation device comprises two electronic sensors for stereoscopic examination of the eye.

14. The ophthalmoscope according to claim 1, and further comprising:
a light source and an image sensor for examining the eye.

15. The ophthalmoscope according to claim 1, and further comprising:
a mirror arranged such that the coupling of the additional beam in the separate beam path does not take place coaxially with the observation beam such that beam paths of the additional and observation beams are separated in a pupil plane of the eye.

16. The ophthalmoscope according to claim 15, wherein the mirror is arranged so that the additional beam is furthermore not coupled in coaxially with the illumination beam.

17. The ophthalmoscope according to claim 1, wherein the separate beam path is coaxial with a principal axis of the ophthalmoscope.

18. The ophthalmoscope according to claim 1, and further comprising:
a wavelength-dependent beam splitter for coupling in the additional beam.

19. The ophthalmoscope according to claim 1, and further comprising:
a wavelength-independent beam splitter for coupling in the additional beam; and
a blocking filter in the observation beam.

20. The ophthalmoscope according to claim 1, and further comprising:
a polarized light source for generating the additional light beam; and
a polarization-dependent beam splitter for coupling in the additional light beam.

21. The ophthalmoscope according to claim 1, and further comprising:
an interface connected to the drive unit for manual control of the position of the image of the additional beam by a user.

22. The ophthalmoscope according to claim 1, and further comprising:
a blocking filter arranged in front of the electronic sensor that, in conjunction with a suitable light source in the illumination beam path, is operable to observe fluorescent emissions from the background of the eye.

23. The ophthalmoscope according to claim 1, and further comprising:
a dichroic beam splitter and an additional sensor that, in conjunction with a suitable light source in the illumination beam path, are operable to observe fluorescent emissions from the background of the eye.

24. The ophthalmoscope according to claim 23, and further comprising:
a further light source, the light of which is coupled into the observation beam path in order to excite fluorescent emissions from the background of the eye.

25. The ophthalmoscope according to claim 1, wherein the electronic control unit is adapted to calculate transformations between individual images from a series of images recorded by the sensor, to apply these transformations to the images recorded by the sensor and to average the images.

26. The ophthalmoscope according to claim 1, wherein the additional beam is a therapy beam for therapy functions, wherein the optical system is configured for generating a targeting beam that is superimposed on the therapy beam, and wherein the drive unit is adapted to determine a time window, in which the targeting beam is switched on from a quantity that correlates a position of spot generated by the targeting beam in an image field to a start time of shutter movement.

27. The ophthalmoscope according to claim 26, wherein the quantity is a time delay $\tau = y/v$, where y is a coordinate of the targeting beam and v is the speed of the shutter movement in the y direction.

28. The ophthalmoscope according to claim 26, wherein the targeting beam is activated for a duration $T_p$ when the electronic shutter permits observation of a region in which the targeting beam is positioned.

29. The ophthalmoscope according to claim 28, wherein the drive unit is further adapted to generate a square wave pulse sequence, each square wave having a pulse width $T_p$.

30. The ophthalmoscope according to claim 26, wherein, to determine when to activate the targeting beam, the drive unit is adapted to receive an analog or digital position signal of the one or more tiltable mirrors and a synchronization pulse of the shutter movement.

31. The ophthalmoscope according to claim 26, wherein the therapy and targeting beams have different wavelengths.

32. The ophthalmoscope according to claim 21, wherein the interface comprises a joystick.

33. The ophthalmoscope according to claim 1, wherein the quantity is a time delay $\tau=y/v$, where y is a coordinate of the additional beam and v is the speed of the shutter movement in the y direction.

34. The ophthalmoscope according to claim 1, wherein the additional beam is activated for a duration $T_p$ when the electronic shutter permits observation of a region in which the additional beam is positioned.

35. The ophthalmoscope according to claim 34, wherein the drive unit is further adapted to generate a square wave pulse sequence, each square wave having a pulse width $T_p$.

36. The ophthalmoscope according to claim 1, wherein, to determine when to activate the additional beam, the drive unit is adapted to receive an analog or digital position signal of the one or more tiltable mirrors and a synchronization pulse of the shutter movement.

* * * * *